US010842999B2

(12) United States Patent
Ghosh

(10) Patent No.: US 10,842,999 B2
(45) Date of Patent: Nov. 24, 2020

(54) MONITORING OF HIS BUNDLE PACING CAPTURE DURING VENTRICULAR PACING THERAPY

(71) Applicant: Medtronic, Inc., Minneapolis, MN (US)

(72) Inventor: Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 174 days.

(21) Appl. No.: 15/928,753

(22) Filed: Mar. 22, 2018

(65) Prior Publication Data

US 2019/0290918 A1    Sep. 26, 2019

(51) Int. Cl.
*A61N 1/00* (2006.01)
*A61N 1/37* (2006.01)
(Continued)

(52) U.S. Cl.
CPC ........... *A61N 1/3714* (2013.01); *A61N 1/025* (2013.01); *A61N 1/3684* (2013.01);
(Continued)

(58) Field of Classification Search
CPC ...... A61N 1/3714; A61N 1/362; A61N 1/371; A61N 1/3712; A61N 1/368;
(Continued)

(56) References Cited

U.S. PATENT DOCUMENTS

| 4,428,378 A | 1/1984 | Anderson et al. |
| 5,052,388 A | 10/1991 | Sivula et al. |

(Continued)

FOREIGN PATENT DOCUMENTS

EP    1110580 A2    6/2001

OTHER PUBLICATIONS

Kamath, G.S., et al. The Utility of 12-Lead Holter Monitoring in Patients With Permanent Atrial Fibrillation for the Identification of Nonresponders After Cardiac Resynchronization Therapy. JACC vol. 53, No. 12, Mar. 24, 2009:1050-5.
(Continued)

*Primary Examiner* — Scott M. Getzow
(74) *Attorney, Agent, or Firm* — Mueting Raasch Group

(57) ABSTRACT

A method and system for delivering a cardiac pacing therapy that includes a cardiac signal being sensed via electrodes of an atrial lead, and an occurrence of one of an intrinsic and a paced atrial depolarization event of a current cardiac cycle being determined in response to the sensed cardiac signal. A first pacing therapy is delivered during the current cardiac cycle in response to the determined occurrence of the depolarization event, and an amplitude of the cardiac signal within the current cardiac cycle subsequent to the delivered first pacing therapy is compared to a predetermined amplitude threshold. A second pacing therapy is delivered, via a left ventricular lead, within the same cardiac cycle and subsequent to the delivered first pacing therapy in response to the amplitude not being more negative than the predetermined amplitude threshold and is not delivered in response to the amplitude being more negative than the predetermined amplitude threshold.

38 Claims, 7 Drawing Sheets

(51) Int. Cl.
   *A61N 1/372*  (2006.01)
   *A61N 1/02*   (2006.01)
   *A61N 1/368*  (2006.01)
   *A61N 1/365*  (2006.01)
   A61N 1/362    (2006.01)
   A61N 1/375    (2006.01)

(52) U.S. Cl.
   CPC ..... *A61N 1/36507* (2013.01); *A61N 1/36585* (2013.01); *A61N 1/37235* (2013.01); *A61N 1/3627* (2013.01); *A61N 1/3756* (2013.01); *A61N 1/37282* (2013.01)

(58) Field of Classification Search
   CPC .. A61N 1/36585; A61N 1/3684; A61N 1/025; A61N 1/37235; A61N 1/37282; A61N 1/3756; A61N 1/3627; A61N 1/365; A61N 1/36507
   See application file for complete search history.

(56) References Cited

U.S. PATENT DOCUMENTS

| | | | |
|---|---|---|---|
| 5,776,168 | A | 7/1998 | Gunderson |
| 5,999,850 | A | 12/1999 | Dawson et al. |
| 6,044,296 | A | 3/2000 | Zhu et al. |
| 6,609,027 | B2 | 8/2003 | Kroll et al. |
| 6,718,206 | B2 | 4/2004 | Casavant |
| 7,139,610 | B2 | 11/2006 | Ferek-Petric |
| 7,187,972 | B1 | 3/2007 | Fain et al. |
| 7,684,863 | B2 | 3/2010 | Parikh et al. |
| 7,738,954 | B1 | 6/2010 | Kroll et al. |
| 8,145,308 | B2 | 3/2012 | Sambelashvili et al. |
| 8,406,899 | B2 | 3/2013 | Kroll et al. |
| 8,560,068 | B2 | 10/2013 | Forslund et al. |
| 8,565,880 | B2 | 10/2013 | Dong et al. |
| 8,634,919 | B1 | 1/2014 | Hou et al. |
| 8,761,880 | B2 | 2/2014 | Maskara et al. |
| 8,670,842 | B1 | 3/2014 | Bornzin et al. |
| 8,738,132 | B1 | 5/2014 | Ghosh et al. |
| 8,750,998 | B1 | 6/2014 | Ghosh et al. |
| 8,750,999 | B1 | 6/2014 | Ghosh et al. |
| 8,781,605 | B2 | 7/2014 | Bornzin et al. |
| 8,942,805 | B2 | 1/2015 | Shuros et al. |
| 8,954,147 | B2 | 2/2015 | Arcot-Krisnamurthy et al. |
| 9,002,454 | B2 | 4/2015 | Ghosh et al. |
| 9,008,777 | B2 | 4/2015 | Dianaty et al. |
| 9,017,341 | B2 | 4/2015 | Bornzin et al. |
| 9,061,157 | B2 | 6/2015 | Ghosh et al. |
| 9,320,905 | B2 | 4/2016 | Ghosh et al. |
| 9,586,050 | B2 | 3/2017 | Ghosh et al. |
| 9,604,064 | B2 | 3/2017 | Ghosh et al. |
| 2004/0215259 | A1 | 10/2004 | Krig et al. |
| 2011/0230922 | A1 | 9/2011 | Fischel |
| 2011/0319951 | A1 | 12/2011 | More et al. |
| 2012/0101539 | A1 | 4/2012 | Zhu et al. |
| 2012/0109235 | A1* | 5/2012 | Sheldon ............... A61N 1/371 607/4 |
| 2012/0165897 | A1 | 6/2012 | Enrooth et al. |
| 2014/0172035 | A1 | 6/2014 | Shuros et al. |
| 2014/0277239 | A1 | 9/2014 | Maskara et al. |
| 2014/0277246 | A1 | 9/2014 | Lu et al. |
| 2014/0277247 | A1 | 9/2014 | Stadler et al. |
| 2015/0088155 | A1 | 3/2015 | Stahmann et al. |
| 2016/0114161 | A1 | 4/2016 | Amblard et al. |
| 2016/0114162 | A1 | 4/2016 | Sheldon et al. |
| 2016/0114168 | A1 | 4/2016 | Sheldon et al. |
| 2016/0114169 | A1 | 4/2016 | Sheldon et al. |
| 2016/0250478 | A1 | 9/2016 | Greenhut et al. |
| 2016/0310722 | A1 | 10/2016 | Demmer |
| 2016/0310726 | A1 | 10/2016 | Demmer et al. |
| 2017/0028194 | A1 | 2/2017 | Bonner et al. |
| 2019/0022378 | A1* | 1/2019 | Prillinger ............. A61N 1/0565 |
| 2019/0275329 | A1* | 9/2019 | Brisben ............... A61N 1/3621 |

OTHER PUBLICATIONS

International Patent Application No. PCT/US2014/028108, filed Mar. 14, 2014; International Search Report and Written Opinion dated Jun. 4, 2014; 13 pages.

Yuyun et al., "His Bundle Pacing: State of the Art," *US Cardiology*, Jan. 2017; 12(1):57-65.

International Patent Application No. PCT/US2019/023535, filed Mar. 22, 2019; International Search Report and Written Opinion dated Jun. 7, 2019; 13 pages.

* cited by examiner

MONITORING OF HIS BUNDLE PACING CAPTURE DURING VENTRICULAR PACING THERAPY

FIELD

The present disclosure pertains to cardiac pacing methods and systems, and, more particularly, to a method and apparatus for delivering continuous ventricular pacing therapy in an implantable medical device.

BACKGROUND

Cardiac resynchronization therapy devices operate by either delivering pacing stimulus to both ventricles or to one ventricle with the desired result of a more or less simultaneous mechanical contraction and ejection of blood from the ventricles. Ideally, each pacing pulse stimulus delivered to a ventricle evokes a response from the ventricle. Delivering electrical stimuli that causes the ventricle to respond is commonly referred to as capturing a ventricle.

For a variety of reasons, cardiac pacing systems may not effectively capture a ventricle. For example, a pacing lead and/or electrode may not be placed in an optimal location. Sensed atrioventricular delay (SAV), paced atrioventricular delay (PAV), right ventricular pre-excitation may also affect whether a ventricle is effectively captured. Additionally, after the medical device has been implanted, migration or dislodgement of the pacing lead may occur. It is desirable to develop additional systems and methods that automatically determine optimal effective capture of a ventricle.

SUMMARY

The present disclosure is directed to a method and device for delivering His Bundle pacing to produce a more normalized and physiologic activation of a patient's heart. The pacing apparatus includes pacing leads extending from a pacing device that lead to prescribed positions in the atria, AV septum and one or both ventricles of the heart. The distal end of the pacing leads include electrodes for sensing cardiac signals and for delivering electrical impulses or pacing therapy. The pacing leads leading to the atria and ventricles are programmed to deliver electrical pulses, on a demand mode basis, if natural electrical signals are not measured within a predetermined period of time.

The pacing lead positioned along the AV septum delivers continuous electrical pulses to the His Bundle immediately following the sensing of atrial activity. These electrical pulses then travel through the right and left bundle branches and to the Purkinje fibers causing the ventricles to depolarize and contract. By delivering such His Bundle pacing to stimulate this natural conduction system, the ventricles contract in a more coordinated manner as compared to delivering ventricular pacing directly to one of the left and right ventricle, thus improving cardiac output and performance. However, while His Bundle pacing tends to result in a more normalized contraction compared to delivering pacing directly within the ventricles, certain factors associated with His Bundle pacing, such as increased tendencies for thresholds to change and an increased tendency for there being contact issues, tend to cause maintaining capture during His Bundle pacing to be a more significant challenge. At the same time, current indications seem to suggest that in order to optimize the effects of resynchronization therapy, it is desirable that the pacing therapy be delivered as close to 100 percent of the time as possible. Therefore, any percentage loss of delivered pacing, such as when the pacing does not result in capturing the heart, may be considered to be less than optimal.

In an implantable medical device according to an example of the present disclosure an atrial lead is positioned near the AV nodal/high septal area to deliver His Bundle pacing therapy, and a second lead may be located in the right ventricle or in the left ventricle. The implantable medical device determines, on a beat-by-beat basis, whether the delivered His Bundle pacing is capturing the patient's heart. If, for a current cardiac cycle or beat, the His Bundle pacing therapy does not capture the patient's heart, the device delivers pacing therapy via the other ventricular lead during the same cardiac cycle at a pre-specified delay from the delivered His Bundle pacing, thereby addressing the loss of capture from the His Bundle pacing during the same cardiac cycle and providing continuous pacing therapy to the patient. On the other hand, if the His Bundle pacing captures the patient's heart, delivery of pacing therapy from the other ventricular lead is prohibited, thereby promoting His Bundle pacing and a more physiologic activation of the ventricles.

According to one example of the present disclosure, a method for delivering a cardiac pacing therapy to a patient comprises: sensing a cardiac signal of the patient; determining an occurrence of one of an intrinsic and a paced atrial depolarization event of a current cardiac cycle in response to the sensed cardiac signal; delivering a first pacing therapy during the current cardiac cycle in response to the determined occurrence of the depolarization event; comparing an amplitude of the cardiac signal within the current cardiac cycle subsequent to the delivered first pacing therapy to a predetermined amplitude threshold; and determining whether to deliver a second pacing therapy within the current cardiac cycle and subsequent to the delivered first pacing therapy in response to the comparing.

According to another example of the present disclosure, a system for delivering a cardiac pacing therapy to a patient comprises: a first cardiac lead having a distal end; at least one electrode positioned at the distal end of the first cardiac lead to sense a cardiac signal of the patient and deliver a first cardiac pacing therapy; a second cardiac lead having a distal end; at least one electrode positioned at the distal end of the second cardiac lead to deliver a second cardiac pacing therapy; and a processor configured to determine an occurrence of one of an intrinsic and a paced atrial depolarization event of a current cardiac cycle in response to the sensed cardiac signal, deliver a first pacing therapy via the at least one electrode of the first cardiac lead during the current cardiac cycle in response to the determined occurrence of the depolarization event, compare an amplitude of the cardiac signal within the current cardiac cycle subsequent to the delivered first pacing therapy to a predetermined amplitude threshold, and determine whether to deliver a second pacing therapy within the current cardiac cycle and subsequent to the delivered first pacing therapy via the at least one electrode of the second cardiac lead in response to the comparing.

In another example of the present disclosure a non-transitory computer readable medium storing instructions which cause a cardiac medical device to perform a method comprises: sensing a cardiac signal of the patient; determining an occurrence of one of an intrinsic and a paced atrial depolarization event of a current cardiac cycle in response to the sensed cardiac signal; delivering a first pacing therapy during the current cardiac cycle in response to the determined occurrence of the depolarization event; comparing an amplitude of the cardiac signal within the current cardiac cycle subsequent to the delivered first pacing therapy to a predetermined amplitude threshold; and determining whether to deliver a second pacing therapy within the current cardiac cycle and subsequent to the delivered first pacing therapy in response to the comparing.

DETAILED DESCRIPTION OF EXEMPLARY EMBODIMENTS

It will be apparent to a skilled artisan that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale.

Figure 1:
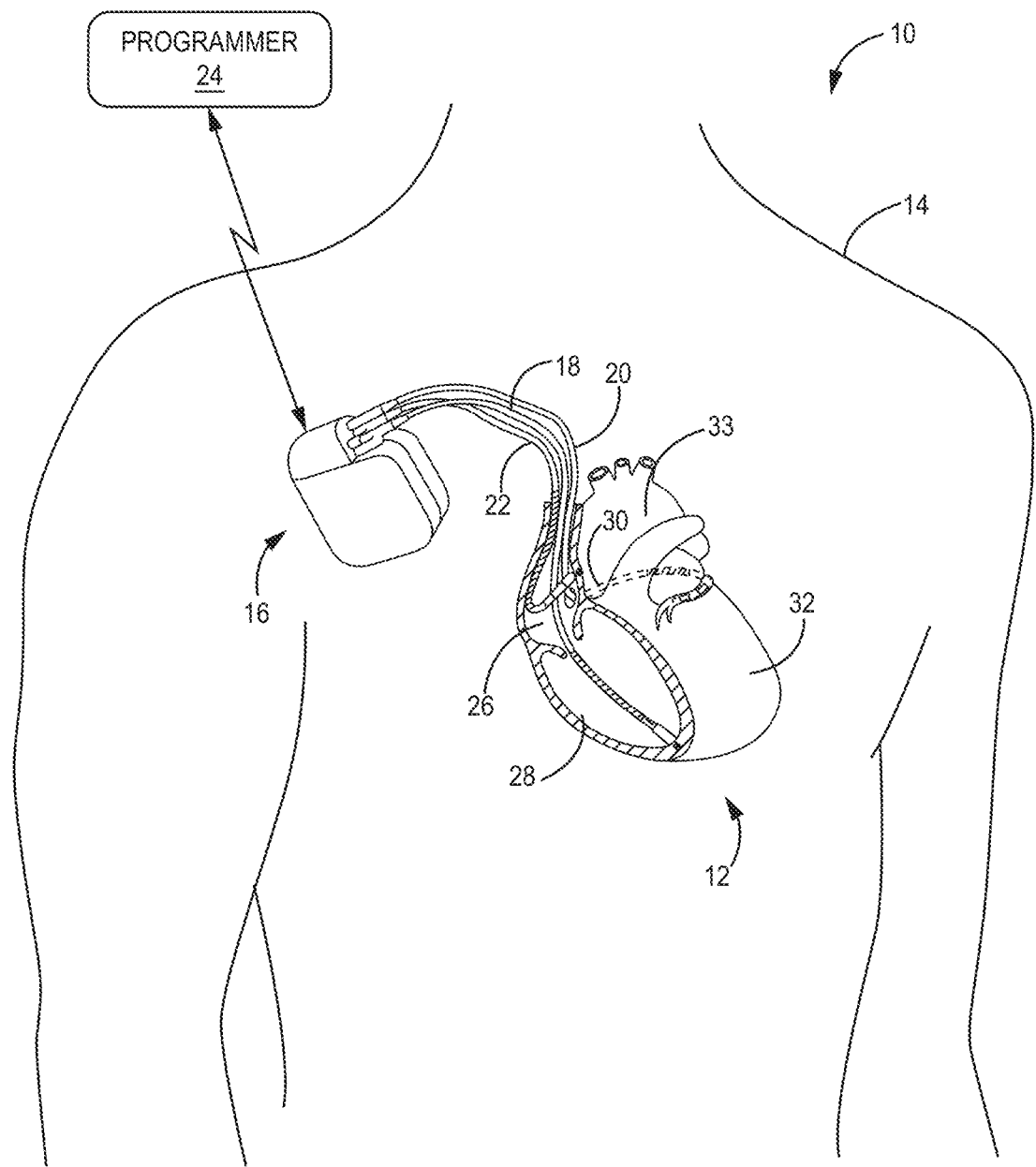
FIG. 1 is a schematic diagram of an exemplary cardiac therapy delivery system that may be used to deliver a pacing therapy according to the present disclosure.

FIG. 1 is a schematic diagram of an exemplary cardiac therapy delivery system that may be used to deliver a pacing therapy according to the present disclosure. The therapy delivery system 10 may include an implantable medical device 16 (IMD), which may be coupled to leads 18, 20, 22 and a programmer 24. The IMD 16 may be, e.g., an implantable pacemaker, cardioverter, and/or defibrillator, that provides electrical signals to the heart 12 of a patient 14 via electrodes coupled to one or more of the leads 18, 20, 22. Patient 14 may, but not necessarily, be a human.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12. In one example, the atrial lead 22 is positioned near the AV nodal/septal area for delivery of His bindle pacing and at least one the ventricle lead 18 is positioned in the right ventricle or the ventricle lead 20 is positioned in the left ventricle, as described below.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., pulse wide, amplitude, voltage, burst length, etc. Further, the IMD 16 may be operable to use various electrode configurations to deliver pacing therapy, which may be unipolar or bipolar. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

In some examples, a programmer 24, which may be a handheld computing device or a computer workstation, may be used by a user, such as a physician, technician, another clinician, and/or patient, to communicate with the IMD 16 (e.g., to program the IMD 16). For example, the user may interact with the programmer 24 to retrieve information concerning one or more detected or indicated faults associated within the IMD 16 and/or the pacing therapy delivered therewith. The IMD 16 and the programmer 24 may communicate via wireless communication using any techniques known in the art. Examples of communication techniques may include, e.g., low frequency or radiofrequency (RF) telemetry, but other techniques are also contemplated.

Figure 2:
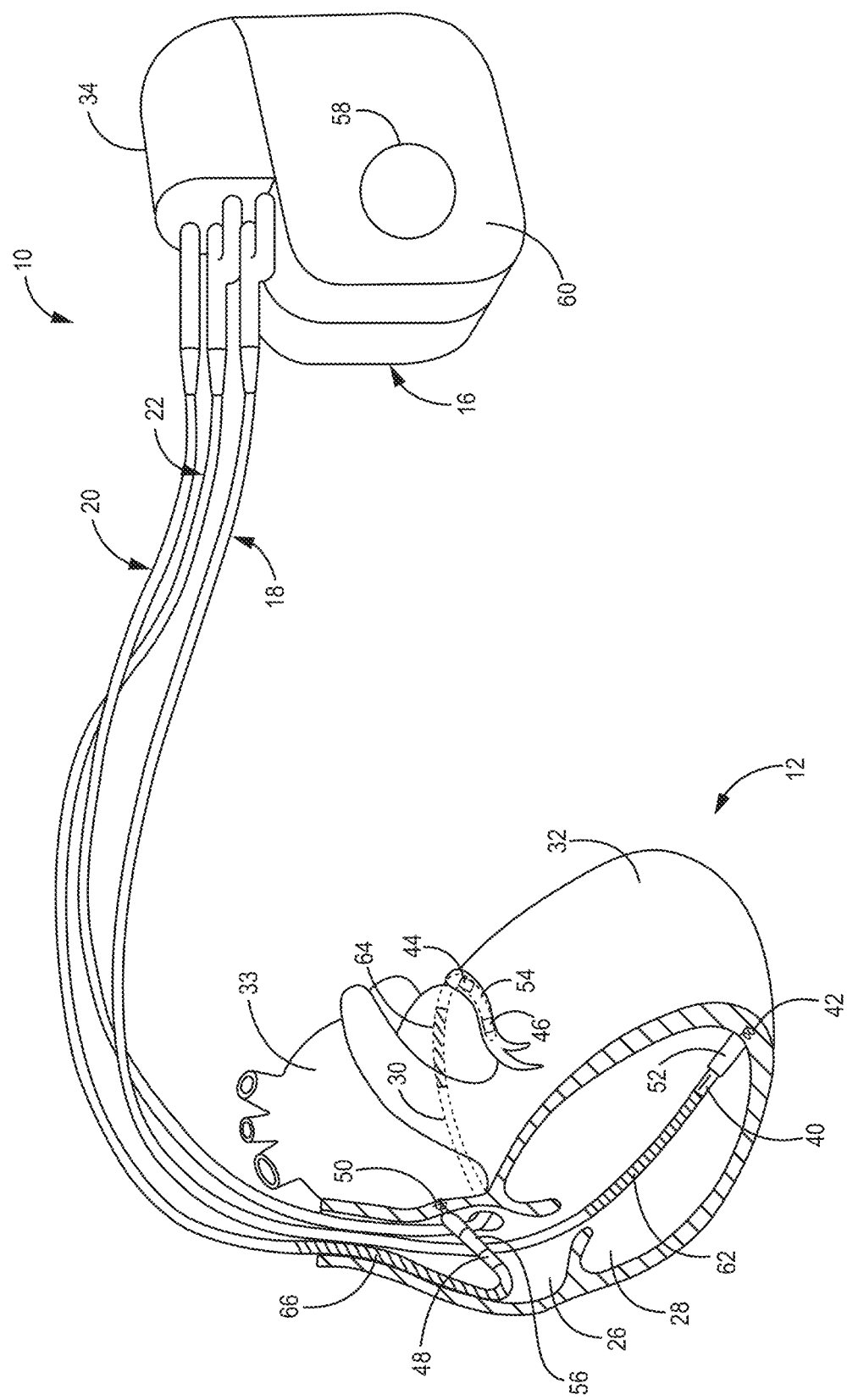
FIG. 2 is a schematic diagram illustrating the exemplary cardiac therapy delivery system of FIG. 1 in more detail.

FIG. 2 is a schematic diagram illustrating the exemplary cardiac therapy delivery system of FIG. 1 in more detail. The leads 18, 20, 22 may be electrically coupled to a therapy delivery module (e.g., for delivery of pacing therapy), a sensing module (e.g., one or more electrodes to sense or monitor electrical activity of the heart 12 for use in determining effectiveness of pacing therapy), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, the bipolar electrodes 44, 46 are located proximate to a distal end of the lead 20 and the bipolar electrodes 48, 50 are located proximate to a distal end of the lead 22.

The electrodes 40, 44, 48 may take the form of ring electrodes, and the electrodes 42, 46, 50 may take the form of extendable helix tip electrodes mounted retractably within the insulative electrode heads 52, 54, 56, respectively. Each of the electrodes 40, 42, 44, 46, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22.

The electrodes 40, 42, 44, 46, 48, 50 may further be used to sense electrical signals (e.g., morphological waveforms within electrograms (EGM)) attendant to the depolarization and repolarization of the heart 12. The sensed electrical signals are conducted to the IMD 16 via the respective leads 18, 20, 22. In some examples, the IMD 16 may also deliver pacing pulses via the electrodes 40, 42, 44, 46, 48, 50 to cause depolarization of cardiac tissue of the patient's heart 12. In some examples, as illustrated in FIG. 2, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 46, 48, 50 may be used for unipolar sensing or pacing in combination with housing electrode 58. In other words, any of electrodes 40, 42, 44, 46, 48, 50, 58 may be used in combination to form a sensing vector, e.g., a sensing vector that may be used to evaluate and/or analysis the effectiveness of pacing therapy. An example of a configuration sensing and pacing may be seen with respect to U.S. Pat. Application No. 61/580,058 filed Dec. 23, 2011, and assigned to the assignee of the present invention, the disclosure of which is incorporated by reference in its entirety herein as modified by preferably using a LVtip (i.e. electrode 46)-Rvcoil (i.e. electrode 62) for the pacing vector and the sensing vector. It is generally understood by those skilled in the art that other electrodes can also be selected as pacing and sensing vectors. Electrode 44 and 64 refer to the third and fourth LV electrodes in the claims.

As described in further detail with reference to FIGS. 3 and 4, the housing 60 may enclose a therapy delivery module that may include a stimulation generator for generating cardiac pacing pulses and defibrillation or cardioversion shocks, as well as a sensing module for monitoring the patient's heart rhythm. The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity during pacing therapy (e.g., for use in analyzing pacing therapy effectiveness) and may be used in combination with any of electrodes 40, 42, 44, 46, 48, 50, 58. In at least one embodiment, the RV elongated electrode 62 may be used to sense electrical activity of a patient's heart during the delivery of pacing therapy (e.g., in combination with the housing electrode 58 forming a RV elongated, coil, or defibrillation electrode-to-housing electrode vector).

The configuration of the exemplary therapy delivery system 10 illustrated in FIGS. 1-2 is merely one example. In one example, the atrial lead 22 is positioned near the AV nodal/septal area for delivery of His bindle pacing and either the ventricle lead 18 is positioned in the right ventricle or the ventricle lead 20 positioned in the left ventricle, or both ventricle leads 18 and 20 may be included, as described below. In addition, the electrode 50 of lead 22 may take the form of a helical tip electrode to enable the lead to be fixedly engaged near the AV nodal/septal area for delivery of His bindle pacing, described below.

Figure 3:
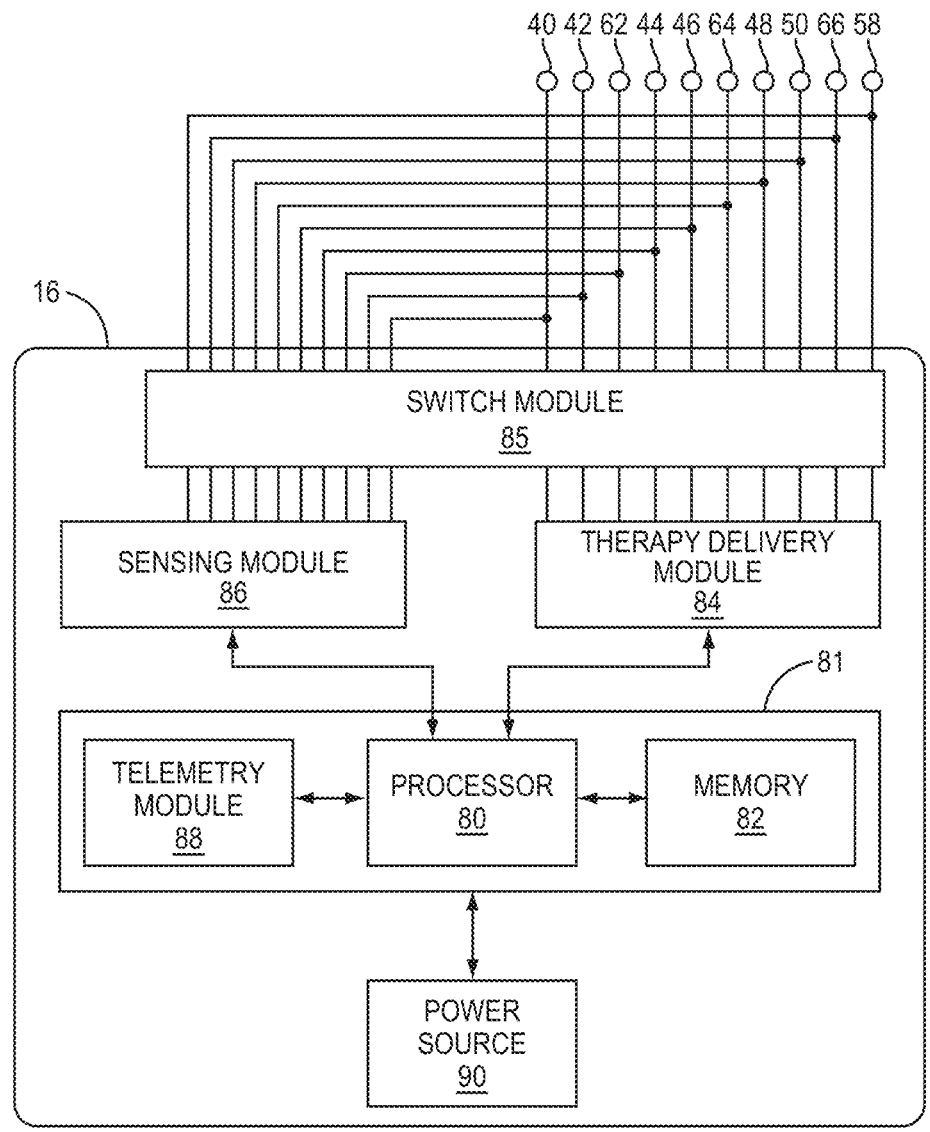
FIG. 3 is an exemplary functional block diagram of an exemplary configuration of an implantable medical device according to an example of the present disclosure.

FIG. 3 is a functional block diagram of an exemplary configuration of an implantable medical device according to an example of the present disclosure. As illustrated in FIG. 3, the IMD 16 may include a control module 81, a therapy delivery module 84 (e.g., which may include a stimulation generator), a sensing module 86, and a power source 90. The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media. Memory 82 includes computer instructions related to capture management, including the method of capture management according to the present disclosure, described in detail below.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control the therapy delivery module 84 to deliver electrical stimulus such as, e.g., pacing pulses with the amplitudes, pulse widths, frequency, or electrode polarities specified by the selected one or more therapy programs (e.g., pacing therapy programs, pacing recovery programs, capture management programs, etc.). As shown, the therapy delivery module 84 is electrically coupled to electrodes 40, 42, 44, 46, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 46, 48, 50, 58, 62, 64, 66.

For example, therapy delivery module 84 may deliver pacing stimulus (e.g., pacing pulses) via ring electrodes 40, 44, 48 coupled to leads 18, 20, and 22, respectively, and/or helical tip electrodes 42, 46, and 50 of leads 18, 20, and 22, respectively. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 46, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 46, 48, 50, 58, 62, 64, 66 to monitor electrical activity of the heart 12, e.g., electrocardiogram (ECG)/electrogram (EGM) signals, etc. The ECG/EGM signals may be used to analyze of a plurality of paced events. More specifically, one or more morphological features of each paced event within the ECG/EGM signals may be used to determine whether each paced event has a predetermined level of effectiveness. The ECG/EGM signals may be further used to monitor heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used to, e.g., sense electrical activity of the patient's heart (e.g., one or more electrical vectors of the patient's heart using any combination of the electrodes 40, 42, 44, 46, 48, 50, 58, 62, 64, 66). In some examples, the control module 81 may select the electrodes that function as sensing electrodes via the switch module within the sensing module 86, e.g., by providing signals via a data/address bus. In some examples, the sensing module 86 may include one or more sensing channels, each of which may include an amplifier.

In some examples, sensing module 86 includes a channel that includes an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an EGM. In some examples, the storage of such EGMs in memory 82 may be under the control of a direct memory access circuit. The control module 81 (e.g., using the processor 80) may employ digital signal analysis techniques to characterize the digitized signals stored in memory 82 to analyze and/or classify one or more morphological waveforms of the EGM signals to determine pacing therapy effectiveness. For example, the processor 80 may be configured to determine, or obtain, one more features of one or more sensed morphological waveforms within one of more electrical vectors of the patient's heart and store the one or more features within the memory 82 for use in determining effectiveness of pacing therapy at a later time.

If IMD 16 is configured to generate and deliver pacing pulses to the heart 12, the control module 81 may include a pacer timing and control module, which may be embodied as hardware, firmware, software, or any combination thereof. The pacer timing and control module may include one or more dedicated hardware circuits, such as an ASIC, separate from the processor 80, such as a microprocessor, and/or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within control module 81 may include atrial and ventricular pacing escape intervals, refractory periods during which sensed P-waves and R-waves are ineffective to restart timing of the escape intervals, and/or the pulse widths of the pacing pulses. As another example, the pacer timing and control module may define a blanking period and provide signals from sensing module 86 to blank one or more channels, e.g., amplifiers, for a period during and after delivery of electrical stimulation to the heart 12. The durations of these intervals may be determined in response to stored data in memory 82. The pacer timing and control module of the control module 81 may also determine the amplitude of the cardiac pacing pulses.

During pacing, escape interval counters within the pacer timing/control module may be reset upon sensing of R-waves and P-waves. Therapy delivery module 84 (e.g., including a stimulation generator) may include one or more pacing output circuits that are coupled, e.g., selectively by the switch module 85, to any combination of electrodes 40, 42, 44, 46, 48, 50, 58, 62, or 66 appropriate for delivery of a bipolar or unipolar pacing pulse to one of the chambers of heart 12. The control module 81 may reset the escape interval counters upon the generation of pacing pulses by therapy delivery module 84, and thereby control the basic timing of cardiac pacing functions, including anti-tachyarrhythmia pacing.

In some examples, the control module 81 may operate as an interrupt driven device and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as the programmer 24 as described herein with respect to FIG. 1. For example, under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer. In at least one embodiment, the telemetry module 88 may be configured to transmit an alarm, or alert, if the pacing therapy becomes ineffective or less effective (e.g., does not have a predetermined level of effectiveness).

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 4:
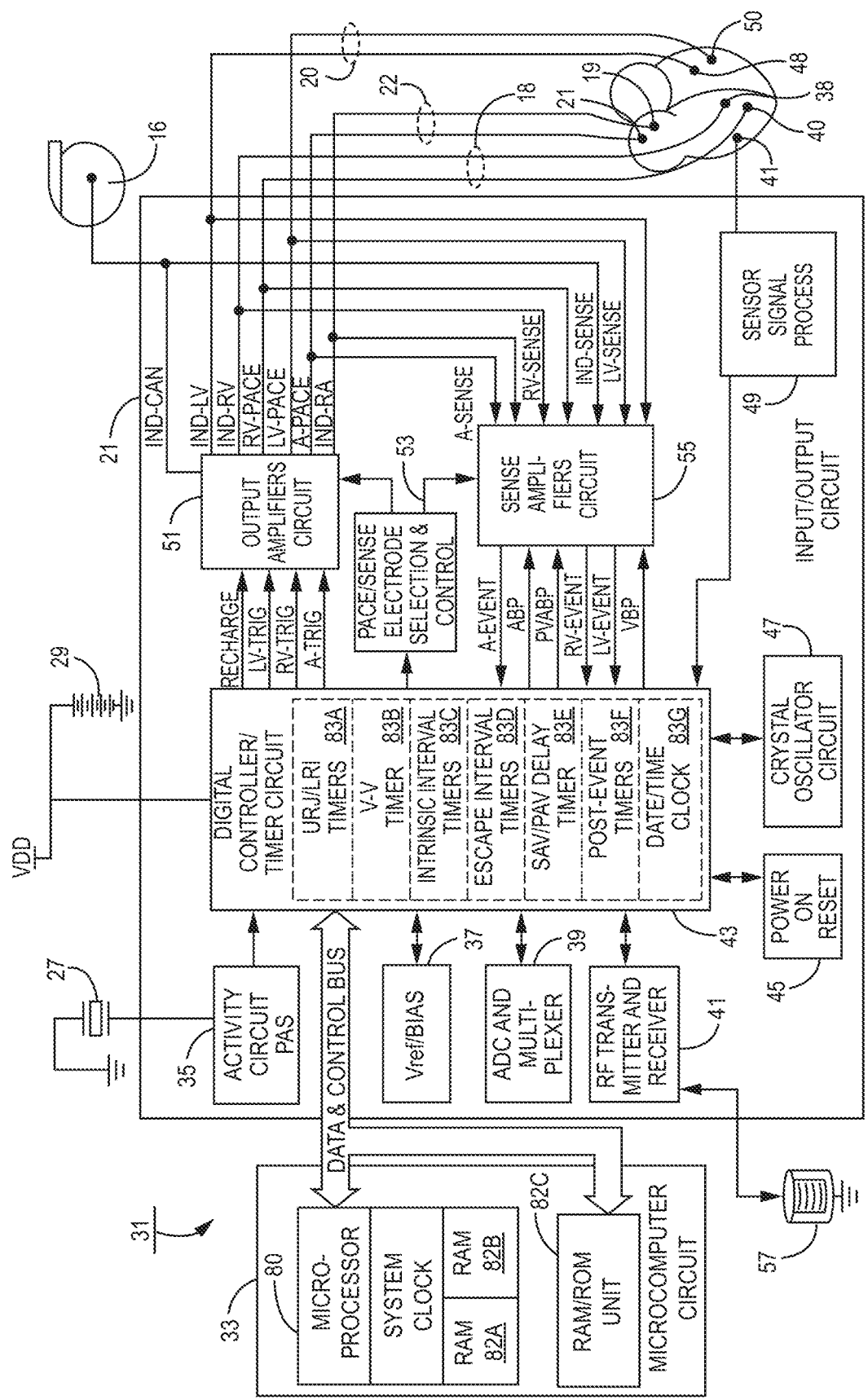
FIG. 4 is an exemplary functional block diagram of circuitry of an implantable medical device according to the present disclosure.

FIG. 4 is an exemplary functional block diagram of circuitry of an implantable medical device according to the present disclosure. FIG. 4 depicts bipolar RA lead 22, bipolar RV lead 18, and bipolar LV CS lead 20 without the LA CS pace/sense electrodes 28 and 30 coupled with an implantable pulse generator (IPG) circuit 31 having programmable modes and parameters of a bi-ventricular DDD/R type known in the pacing art. In turn, the sensor signal processing circuit 43 indirectly couples to the timing circuit 83 and via data and control bus to microcomputer circuitry 33. The IPG circuit 31 is illustrated in a functional block diagram divided generally into a microcomputer circuit 33 and a pacing circuit 83. The pacing circuit 83 includes the digital controller/timer circuit 83, the output amplifiers circuit 51, the sense amplifiers circuit 55, the RF telemetry transceiver 41, the activity sensor circuit 35 as well as a number of other circuits and components described below.

Crystal oscillator circuit 47 provides the basic timing clock for the pacing circuit 320, while battery 29 provides power. Power-on-reset circuit 45 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 320, while analog to digital converter ADC and multiplexer circuit 39 digitizes analog signals and voltage to provide real time telemetry of cardiac signals from sense amplifiers 55, for uplink transmission via RF transmitter and receiver circuit 41. Voltage reference and bias circuit 37, ADC and multiplexer 39, power-on-reset circuit 45 and crystal oscillator circuit 47 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 35 in the depicted, exemplary IPG circuit 31. The patient activity sensor 316 is coupled to the IPG housing and may take the form of a piezoelectric crystal transducer as is well known in the art and its output signal is processed and used as the RCP. Sensor 316 generates electrical signals in response to sensed physical activity that are processed by activity circuit 35 and provided to digital controller/timer circuit 83. Activity circuit 35 and associated sensor 316 may correspond to the circuitry disclosed in U.S. Pat. Nos. 5,052,388 and 4,428,378. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Data transmission to and from the external programmer is accomplished by means of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 83 and A-EVENT, RV-EVENT, and LV-EVENT signals generated by sense amplifiers circuit 55, among others. The specific values of the intervals and delays timed out by digital controller/timer circuit 83 are controlled by the microcomputer circuit 33 by means of data and control bus 306 from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals and the energy delivered to each ventricle.

In one embodiment, microprocessor 80 is a custom microprocessor adapted to fetch and execute instructions stored in RAM/ROM unit 314 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 83 operates under the general control of the microcomputer 33 to control timing and other functions within the pacing circuit 320 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 374 for timing post-ventricular time periods, and a date/time clock 376.

The AV delay interval timer 83E is loaded with an appropriate delay interval for one ventricular chamber (i.e., either an A-RVp delay or an A-LVp delay as determined using known methods) to time-out starting from a preceding A-PACE or A-EVENT. The interval timer 83E triggers pacing stimulus delivery, and can based on one or more prior cardiac cycles (or from a data set empirically derived for a given patient).

The post-event timers 374 time out the post-ventricular time periods following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, post-ventricular time periods, and post-atrial time periods that vary with the sensor based escape interval established in response to the RCP(s) and/or with the intrinsic atrial rate.

The output amplifiers circuit 51 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 83 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers corresponding to any of those presently employed in contemporary cardiac pacemakers for atrial and ventricular pacing and sensing. It has been common in the prior art to use very high impedance P-wave and R-wave sense amplifiers to amplify the voltage difference signal which is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the atrial and ventricular sense amplifiers 55.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND_CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND_CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier, if provided, result in a LA-EVENT signal that is communicated to the digital controller/timer circuit 83. Ventricular depolarizations or R-waves in the RV-SENSE signal are sensed by a ventricular sense amplifier result in an RV-EVENT signal that is communicated to the digital controller/timer circuit 83. Similarly, ventricular depolarizations or R-waves in the LV-SENSE signal are sensed by a ventricular sense amplifier result in an LV-EVENT signal that is communicated to the digital controller/timer circuit 83. The RV-EVENT, LV-EVENT, and RA-EVENT, LA-SENSE signals may be refractory or non-refractory and can inadvertently be triggered by electrical noise signals or aberrantly conducted depolarization waves rather than true R-waves or P-waves.

The exemplary methods and/or devices described herein may track, or monitor, the effectiveness of pacing therapy by analyzing one or more features of a sensed morphological waveform corresponding to a paced event for one or more monitored electrical vectors of the patient's heart. As used herein, a sensed morphological waveform may correspond to a paced event by occurring within a predetermined, or selected, time period, or sensing window, (e.g., 200 milliseconds) after the delivery of pacing stimulus. The sensed morphological waveform may, e.g., result from the delivery of pacing stimulus and/or intrinsic conduction.

The present disclosure is directed to a method and device for delivering His Bundle pacing to produce a more normalized and physiologic activation of a patient's heart. The pacing apparatus includes pacing leads extending from a pacing device that lead to prescribed positions in the atria, AV septum and one or both ventricles of the heart. The distal end of the pacing leads include electrodes for sensing cardiac signals and for delivering electrical impulses or pacing therapy. The pacing leads leading to the atria and ventricles are programmed to deliver electrical pulses, on a demand mode basis, if natural electrical signals are not measured within a predetermined period of time.

The pacing lead positioned along the AV septum delivers continuous electrical pulses to the His Bundle immediately following the sensing of atrial activity. These electrical pulses then travel through the right and left bundle branches and to the Purkinje fibers causing the ventricles to depolarize and contract. By delivering such His Bundle pacing to stimulate this natural conduction system, the ventricles contract in a more coordinated manner as compared to delivering ventricular pacing directly to one of the left and right ventricle, thus improving cardiac output and performance. However, while His Bundle pacing tends to result in a more normalized contraction compared to delivering pacing directly within the ventricles, certain factors associated with His Bundle pacing, such as increased tendencies for thresholds to change and an increased tendency for there being contact issues, tend to cause maintaining capture during His Bundle pacing to be a more significant challenge. At the same time, current indications seem to suggest that in order to optimize the effects of resynchronization therapy, it is desirable that the pacing therapy be delivered as close to 100 percent of the time as possible. Therefore, any percentage loss of delivered pacing, such as when the pacing does not result in capturing the heart, may be considered to be less than optimal.

In an implantable medical device according to an example of the present disclosure an atrial lead is positioned near the AV nodal/high septal area to deliver His Bundle pacing therapy, and a second lead may be located in the right ventricle or in the left ventricle. The implantable medical device determines, on a beat-by-beat basis, whether the delivered His Bundle pacing is capturing the patient's heart. If, for a current cardiac cycle or beat, the His Bundle pacing therapy does not capture the patient's heart, the device delivers pacing therapy via the other ventricular lead during the same cardiac cycle at a pre-specified delay from the delivered His Bundle pacing, thereby addressing the loss of capture from the His Bundle pacing during the same cardiac cycle and providing continuous pacing therapy to the patient. On the other hand, if the His Bundle pacing captures the patient's heart, delivery of pacing therapy from the other ventricular lead is prohibited, thereby promoting His Bundle pacing and a more physiologic activation of the ventricles.

Figure 5:
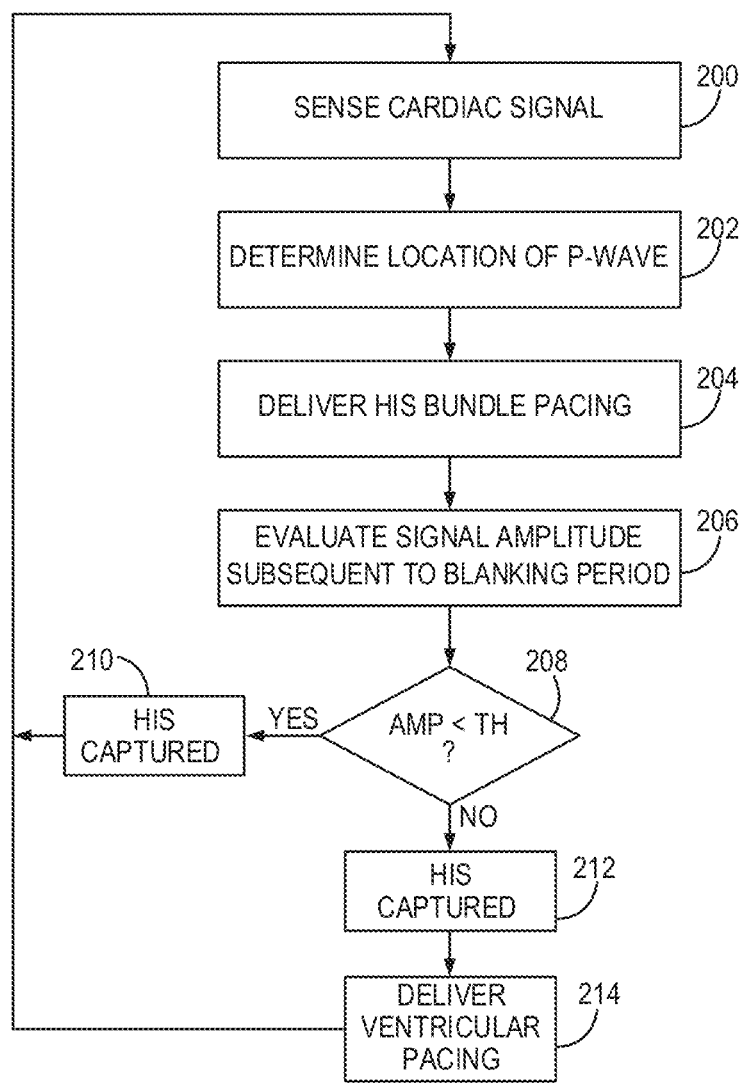
FIG. 5 is a flow chart of a method of delivering a pacing therapy according to an example of the present disclosure.

FIG. 5 is a flowchart of a method of delivering a pacing therapy according to an example of the present disclosure. In one example, the atrial lead 22 may be positioned near the AV nodal/septal area for delivery of His Bundle pacing via electrodes via the tip electrode 50 and ring electrode 48 and either the ventricle lead 18 may be positioned in the right ventricle or the ventricle lead 20 may be positioned in the left ventricle, or both the ventricle lead 18 may be positioned in the right ventricle and the ventricle lead 20 may be positioned in the left ventricle. As illustrated in FIG. 5, during delivery of a pacing therapy according to an example of the present disclosure, a near-field cardiac signal may be sensed, Block 200, via the tip electrode 50 and ring electrode 48 of the atrial lead 22. The processor 80 processes the sensed cardiac signal and determines the location of a P-wave of the sensed cardiac signal, Block 202. The processor 80 causes His Bundle pacing to be delivered, Block 202, via the tip electrode 50 and the ring electrode 48 of the atrial lead 22, based on the location of the determined P-wave. For example, the processor 80 may cause such His Bundle pacing to be delivered at a predetermined time delay from the P-wave, as described below. Upon delivery of the His Bundle pace, Block 204, the processor 80 determines the amplitude of the signal sensed for the same cardiac cycle that occurs immediately after a blanking period associated with the delivered His Bundle pacing, Block 206, and determines whether the amplitude is less than an amplitude threshold, Block 208, as described below.

If the post pace blanking amplitude for the current cardiac cycle is determined to be less than the amplitude threshold, Yes in Block 208, capture is determined to have occurred for the His Bundle pacing therapy delivered for the current cardiac cycle, Block 210, and the process is repeated, Block 200, for the next cardiac cycle. If the post pace blanking amplitude for the current cardiac cycle is not determined to be less than the amplitude threshold, No in Block 208, capture is not determined to have occurred for the current delivered His Bundle pacing therapy, Block 212. When capture does not occur as a result of the delivered His Bundle pacing, Block 212, the processor 80 causes ventricular pacing to be delivered within the same cardiac cycle, Block 214, via either the bipolar electrodes 40, 42 located proximate to the distal end of the right ventricular lead 18, or the bipolar electrodes 44, 46 located proximate to the distal end of the left ventricular lead 20.

In this way, an implantable medical device or implantable medical device system may include an atrial lead positioned near the AV nodal/high septal area to deliver His Bundle pacing therapy, and a second lead located in at least either the right ventricle or in the left ventricle. The processor 80 of the implantable medical device determines, for a given cardiac cycle, whether the delivered His Bundle pacing is capturing the patient's heart for that cardiac cycle. If, during a given single cardiac cycle, the processor 80 determines that the His Bundle pacing therapy does not capture the heart, the processor 80 causes ventricular pacing to be delivered during the same cardiac cycle at a pre-specified delay from the His Bundle pacing delivered during that cycle. If the processor 80 determines that the His Bundle pacing captures the patient's heart, delivery of pacing therapy from the other ventricular lead is prohibited by the processor 80 and the process is repeated for delivery of His Bundle pacing for the next cardiac cycle. The process is then repeated for the next cardiac cycle. As a result, the present disclosure reduces instances where the His Bundle pacing does not capture the heart by delivering ventricular pacing within the same cardiac cycle, rather than allowing the loss of capture to occur and adjusting parameters to address the loss of capture in the subsequent cardiac cycle, resulting in delivery of a more continuous resynchronization pacing therapy to the patient.

Figure 6A:
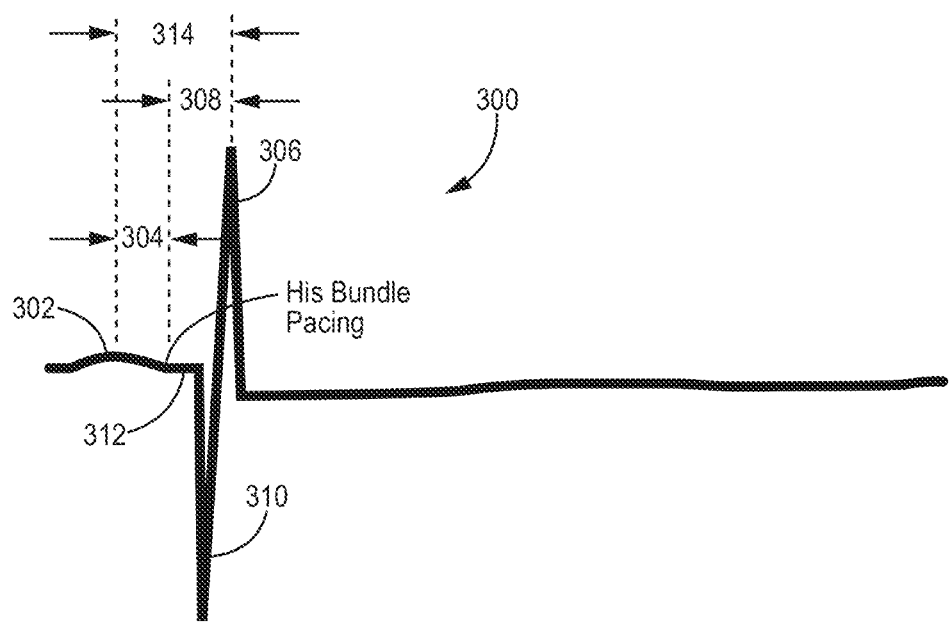
FIGS. 6A-C are graphical representations of delivery of a pacing therapy according to an example of the present disclosure.
Figure 6B:
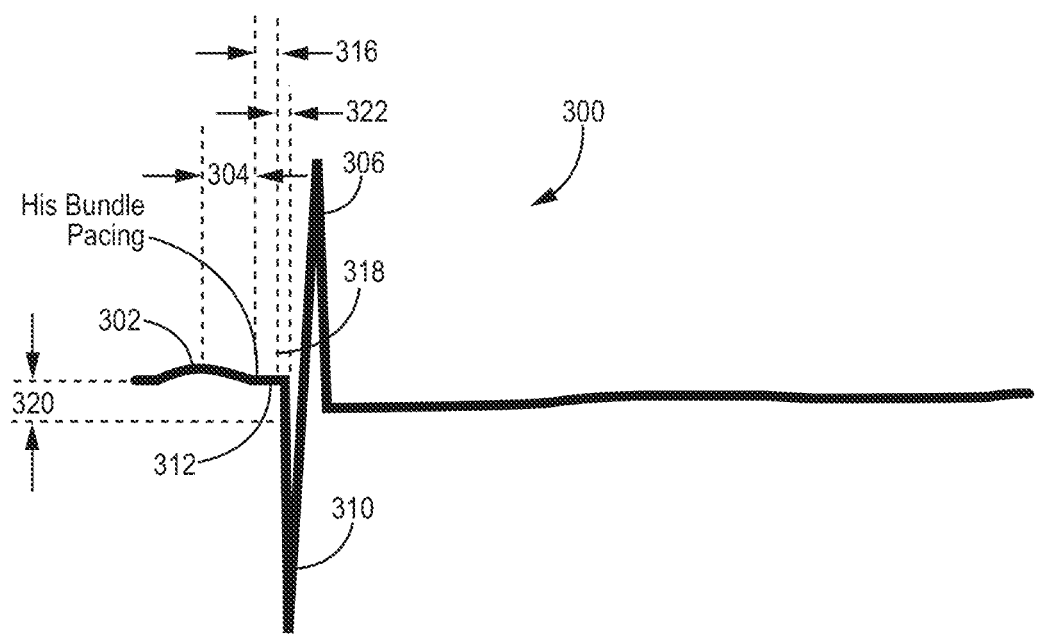
Figure 6C:
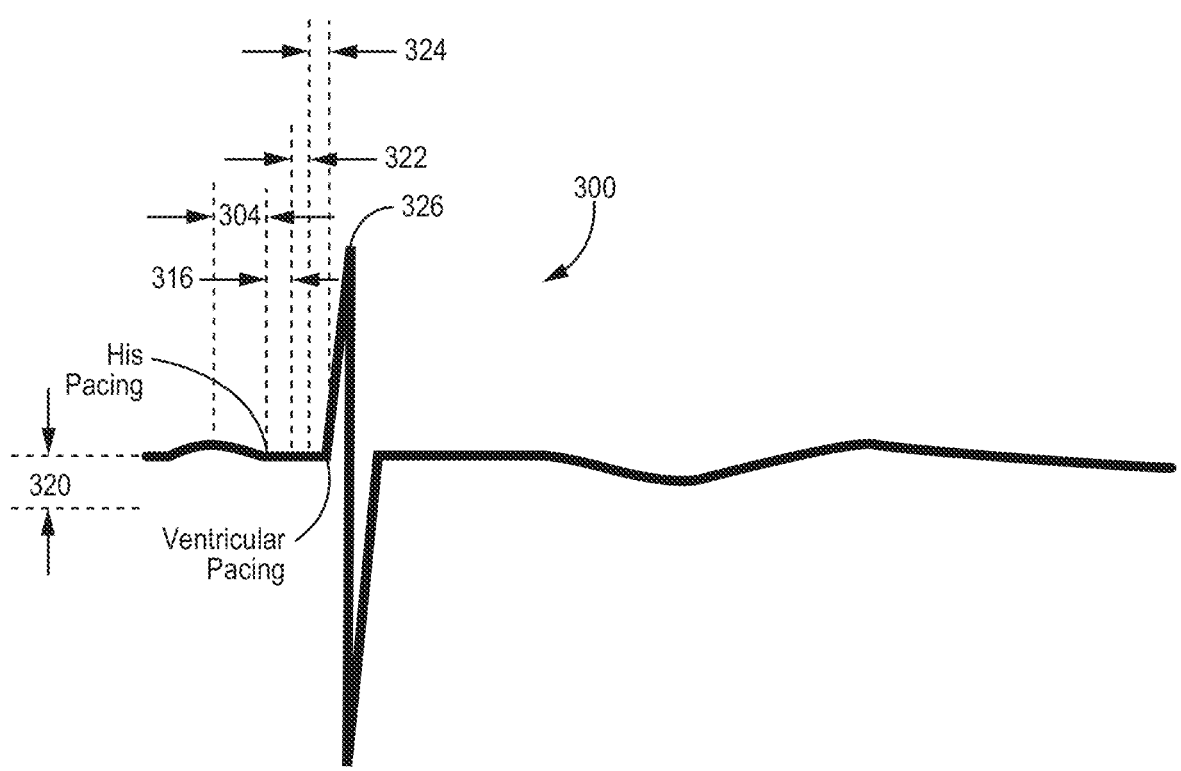

FIGS. 6A-C are graphical representations of delivery of a pacing therapy according to an example of the present disclosure. As illustrated in FIG. 6A, during delivery of pacing therapy the processor 80 senses a cardiac signal 300 via the tip electrode 50 and the ring electrode 48 of the atrial lead 22 and determines the location of a P-wave 302 of the sensed signal 300. Once the location of the P-wave 302 is determined, the processor 80 delivers His Bundle pacing via the tip electrode 50 and the ring electrode 48 of the atrial lead 22 positioned along the His Bundle. The His Bundle pacing is delivered at a predetermined time period or AV delay or interval 304 subsequent to the P-wave 302. If the delivered His Bundle pacing results in capture of the heart, the delivered His Bundle pacing is followed by an evoked response 306 that occurs within a predetermined time period 308 subsequent to the delivery of His bundle pacing.

As illustrated in FIGS. 6A and 6B, during delivering of His Bundle pacing via the tip electrode 50 and the ring electrode 48 of the atrial lead 22, a negative amplitude evoked response 310 of the signal 300 relative to a baseline 312 of the signal 300 occurs subsequent to the delivered His Bundle pacing when the delivered His Bundle pacing results in capture of the patient's heart, i.e., the evoked response 306 occurs. On the other hand, as illustrated in FIG. 6C, such negative amplitude evoked response 310 of the signal 300 relative to a baseline 312 of the signal 300 does not occur subsequent to the delivered His Bundle pacing when the delivered His Bundle pacing does not result in capture of the patient's heart The time period 314 between the P-wave 302 and the evoked response 306 of the His Bundle pacing is patient specific and may depend on the programmed paced AV interval, which is typically programmed to a value between 60 ms and 150 ms in the absence of intrinsic ventricular conduction (due to AV block, for example), or in cases of an intrinsic AV conduction, may be set as a percentage of the patient's intrinsic AV interval (i.e., the timing between the atrial event and the patient's intrinsic conduction). In the presence of the patient's intrinsic AV conduction, an example AV interval may be programmed to be either at least 45 ms, at least 50 ms, at least 55 ms, at least 60 ms, at least 65 ms, for example, prior to an intrinsic ventricular event. Therefore, in an example in which the intrinsic AV interval for the patient is set to be 200 ms, the processor 80 may determine the time period or delay 304 subsequent to the P-wave 302 for delivering the His Bundle pacing as being a percentage, such as 40 percent for example, of the intrinsic AV interval, so that the His Bundle pacing is delivered at least a certain time period before the intrinsic ventricular event, such as at least 60 ms for example. As a result, in one example, the processor 80 may deliver the His Bundle pacing 80 ms (40% of 200 ms=80 ms) after the determined P-wave 302, resulting in the AV delay 304 being 80 ms.

As illustrated in FIG. 6B, after the delivery of the His Bundle pacing, the processor 80 waits for a predetermined time period 316 subsequent to the delivered His Bundle pacing, known as a blanking period. The time period 316 associated with the blanking period is typically programmable, and in one example may be set as 20 ms. Once the blanking period 316 has expired, the processor 80 determines whether an amplitude 310 extending from the baseline 312 of the sensed signal 300 is more negative than a predetermined amplitude threshold 320, such as −5 millivolts for example, during a time period 322 extending subsequent to the end 318 of the blanking period 316. Exemplary values of the time period 322 for determining whether the amplitude is more negative than the amplitude threshold may be between 5 ms and 20 ms, for example.

As illustrated in the example of FIG. 6B, when the amplitude 310 of the sensed signal 300 relative to the baseline 312 within the time period 322 is more negative than the predetermined amplitude threshold 320, the processor 80 determines that the delivered His Bundle pacing resulted in capture of the heart, and the process is repeated for delivering His Bundle pacing during the next cardiac cycle. On the other hand, as illustrated in the example of FIG. 6C, when the processor 80 determines that an amplitude of the sensed signal 300 relative to the baseline 312 within the time period 322 subsequent to the blanking period 316 is not more negative than the predetermined amplitude threshold 320, the processor 80 determines that the delivered His Bundle pacing will likely not result in capture of the heart. Therefore, the processor 80 delivers a ventricular pacing signal via one of the left ventricular lead 20 and the right ventricular lead 18 for the same cardiac cycle within a time period 324 subsequent to expiration of or the end of time period 322, which may be between 5 ms to 10 ms. As a result, after delivering His Bundle pacing, a ventricular pacing event and resulting paced evoked response 326 are generated in the same cardiac cycle if the delivered His Bundle pacing is likely to fail to capture the patient's heart, resulting in continuous pacing therapy being delivered. The second pacing therapy, i.e., the ventricular pacing therapy, may be delivered from one or more pacing leads located in more standard anatomic positions within the ventricle, with outputs that are well above pacing capture thresholds for that particular lead, such as 1 volt above the pacing capture threshold for that lead, for example, in order to maximize the likelihood of effective capture for the cardiac cycle.

In this way, a method for delivering a pacing therapy according to an example of the present disclosure may include the processor 80 sensing a cardiac signal 300 via the tip electrode 50 and the ring electrode 48 of the atrial lead 22 and determining an occurrence of a P-wave 302 of a current cardiac cycle in response to the sensed cardiac signal. The processor 80 causes a first pacing therapy to be delivered via the tip electrode 50 and the ring electrode 48 of the atrial lead 22 during the current cardiac cycle in response to the determined occurrence of the P-wave 302, compares an amplitude of the cardiac signal within the current cardiac cycle subsequent to the delivered first pacing therapy to a predetermined amplitude threshold, and delivers a second pacing therapy via the bipolar electrodes 44, 46 located proximate to the distal end of the left ventricular lead 20 within the same or current cardiac cycle and subsequent to the delivered first pacing therapy in response to the comparing.

For example, the processor 80 may compare the amplitude of the cardiac signal 300 to the amplitude threshold during a first time period 322 subsequent to a blanking period 316 associated with the delivered first pacing therapy, and if the amplitude of the cardiac signal is not more negative than the amplitude threshold 320, deliver the second pacing therapy within a second time interval 324, which may be between 5 ms and 10 ms, for example, subsequent to the first time period 322, wherein a sum of the AV interval 304 at which the His Bundle pacing was delivered, the blanking period 316 subsequent to the delivered His Bundle pacing, the first time period 322 and the second time period 324 is less than the intrinsic AV interval of the patient, or, if intrinsic AV conduction is determined to be absent (due to atrio-ventricular block, for example), a sum of the AV interval 304 at which the His Bundle pacing was delivered, the blanking period 316 subsequent to the delivered His Bundle pacing, the first time period 322 and the second time period 324 is less than the first AV interval plus an additional period of time, such as 40 ms for example.

As a result, the present disclosure reduces instances of loss of capture during His Bundle pacing by delivering ventricular pacing within the same cardiac cycle when the His Bundle pacing fails to capture for that cardiac cycle, rather than allowing the loss of capture to occur and adjusting parameters to address the loss of capture in the subsequent cardiac cycle, resulting in delivery of a more continuous resynchronization pacing therapy to the patient.

The techniques described in this disclosure, including those attributed to the IMD 16, the programmer 24, or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

ILLUSTRATED EMBODIMENTS

Embodiment 1

A method for delivering a cardiac pacing therapy to a patient, comprising:
sensing a cardiac signal of the patient;
determining an occurrence of one of an intrinsic and a paced atrial depolarization event of a current cardiac cycle in response to the sensed cardiac signal;
delivering a first pacing therapy during the current cardiac cycle in response to the determined occurrence of the depolarization event;
comparing an amplitude of the cardiac signal within the current cardiac cycle subsequent to the delivered first pacing therapy to a predetermined amplitude threshold; and
determining whether to deliver a second pacing therapy within the current cardiac cycle and subsequent to the delivered first pacing therapy in response to the comparing.

Embodiment 2

The method of embodiment 1, wherein the first pacing therapy comprises His Bundle pacing and the second pacing therapy comprises ventricular pacing therapy.

Embodiment 3

The method of any of embodiments 1-2, further comprising determining whether intrinsic atrio-ventricular conduction is absent, wherein the first pacing therapy comprises His Bundle pacing and the second pacing therapy comprises ventricular pacing therapy, wherein the His Bundle pacing is delivered having an AV delay between approximately 60 ms and 150 ms in response to intrinsic atrio-ventricular conduction being absent.

Embodiment 4

The method of any of embodiments 1-3, further comprising:
determining to deliver the second pacing therapy in response to the amplitude not being more negative than the predetermined amplitude threshold; and
determining not to deliver the second pacing therapy in response to the amplitude being more negative than the predetermined amplitude threshold.

Embodiment 5

The method of any of embodiments 1-4, wherein the predetermined amplitude threshold is approximately −5 millivolts.

Embodiment 6

The method of any of embodiments 1-5, further comprising:
comparing the amplitude of the cardiac signal to the amplitude threshold during a first time period subsequent to a blanking period associated with the delivered first pacing therapy; and
determining, in response the amplitude of the cardiac signal not being more negative than the amplitude threshold, to deliver the second pacing therapy within a second time period subsequent to the first time period, wherein a sum of an AV interval at which the first pacing therapy is delivered relative to the determined atrial depolarization event, the blanking period, the first time period and the second time period is less than an intrinsic AV interval associated with the patient.

Embodiment 7

The method of embodiment 6, further comprising determining whether intrinsic atrio-ventricular conduction is absent, wherein the first pacing therapy comprises His Bundle pacing and the second pacing therapy comprises ventricular pacing therapy, wherein the sum of the AV interval at which the first pacing therapy is delivered relative to the determined atrial depolarization event, the blanking period, the first time period and the second time period is less than a sum of the AV interval at which the first pacing therapy is delivered relative to the determined atrial depolarization event and 40 ms in response to intrinsic atrio-ventricular conduction being absent.

Embodiment 8

The method of embodiment 7, wherein the first time period is between approximately 5 milliseconds and 20 milliseconds and the second time period is between approximately 5 milliseconds and 10 milliseconds.

Embodiment 9

The method of any of embodiments 1-6, further comprising:
comparing the amplitude of the cardiac signal to the amplitude threshold during a first time period subsequent to a blanking period associated with the delivered first pacing therapy;
determining, in response the amplitude of the cardiac signal not being more negative than the amplitude threshold, to deliver the second pacing therapy within a second time period subsequent to the first time period; and
determining, in response to the amplitude being more negative than the predetermined amplitude threshold, not to deliver the second pacing therapy, wherein the first pacing therapy comprises His Bundle pacing and the second pacing therapy comprises ventricular pacing therapy.

Embodiment 10

The method of embodiment 9, wherein the predetermined amplitude threshold is approximately −5 millivolts.

Embodiment 11

The method of any of embodiments 9-10, wherein a sum of an AV interval at which the first pacing therapy is delivered relative to the determined atrial depolarization event, the blanking period, the first time period, and the second time period is less than an intrinsic AV-interval associated the patient.

Embodiment 12

The method of embodiment 11, wherein the first time period is between approximately 5 milliseconds and 20 milliseconds and the second time period is between approximately 5 milliseconds and 10 milliseconds.

Embodiment 13

A system for delivering a cardiac pacing therapy to a patient, comprising:
a first cardiac lead having a distal end;
at least one electrode positioned at the distal end of the first cardiac lead to sense a cardiac signal of the patient and deliver a first cardiac pacing therapy;
a second cardiac lead having a distal end;
at least one electrode positioned at the distal end of the second cardiac lead to deliver a second cardiac pacing therapy; and
a processor configured to determine an occurrence of one of an intrinsic and a paced atrial depolarization event of a current cardiac cycle in response to the sensed cardiac signal, deliver a first pacing therapy via the at least one electrode of the first cardiac lead during the current cardiac cycle in response to the determined occurrence of the depolarization event, compare an amplitude of the cardiac signal within the current cardiac cycle subsequent to the delivered first pacing therapy to a predetermined amplitude threshold, and determine whether to deliver a second pacing therapy within the current cardiac cycle and subsequent to the delivered first pacing therapy via the at least one electrode of the second cardiac lead in response to the comparing.

Embodiment 14

The system of embodiment 13, wherein the first pacing therapy comprises His Bundle pacing and the second pacing therapy comprises ventricular pacing therapy.

Embodiment 15

The system of any of embodiments 13-14, wherein the processor is configured to determine whether intrinsic atrio-ventricular conduction is absent, wherein the first pacing therapy comprises His Bundle pacing and the second pacing therapy comprises ventricular pacing therapy, and wherein the His Bundle pacing is delivered having an AV delay between approximately 60 ms and 150 ms in response to intrinsic atrio-ventricular conduction being absent.

Embodiment 16

The system of any of embodiments 13-15, wherein the processor is configured to determine to deliver the second pacing therapy in response to the amplitude not being more negative than the predetermined amplitude threshold, and determine not to deliver the second pacing therapy in response to the amplitude being more negative than the predetermined amplitude threshold.

Embodiment 17

The system of embodiment 16, wherein the predetermined amplitude threshold is approximately −5 millivolts.

Embodiment 18

The system of any of embodiments 13-14, wherein the processor is configured to compare the amplitude of the cardiac signal to the amplitude threshold during a first time period subsequent to a blanking period associated with the delivered first pacing therapy, and determine, in response the amplitude of the cardiac signal not being more negative than the amplitude threshold, to deliver the second pacing therapy within a second time period subsequent to the first time period, wherein a sum of an AV interval at which the first pacing therapy is delivered relative to the determined atrial depolarization event, the blanking period, the first time period and the second time period is less than an intrinsic AV interval associated with the patient.

Embodiment 19

The system of embodiment 18, wherein the processor is configured to determine whether intrinsic atrio-ventricular conduction is absent, wherein the first pacing therapy comprises His Bundle pacing and the second pacing therapy comprises ventricular pacing therapy, and wherein the sum of the AV interval at which the first pacing therapy is delivered relative to the determined atrial depolarization event, the blanking period, the first time period and the second time period is less than a sum of the AV interval at which the first pacing therapy is delivered relative to the determined atrial depolarization event and 40 ms in response to intrinsic atrio-ventricular conduction being absent.

Embodiment 20

The system of any of embodiments 18-19, wherein the first time period is between approximately 5 milliseconds and 20 milliseconds and the second time period is between approximately 5 milliseconds and 10 milliseconds.

Embodiment 21

The system of any of embodiments 18-20, wherein the processor is configured to compare the amplitude of the cardiac signal to the amplitude threshold during a first time period subsequent to a blanking period associated with the delivered first pacing therapy, determine, in response the amplitude of the cardiac signal not being more negative than the amplitude threshold, to deliver the second pacing therapy within a second time period subsequent to the first time period, and determine, in response to the amplitude being more negative than the predetermined amplitude threshold, not to deliver the second pacing therapy, wherein the first pacing therapy comprises His Bundle pacing and the second pacing therapy comprises ventricular pacing therapy.

Embodiment 22

The system of embodiment 21, wherein the predetermined amplitude threshold is approximately −5 millivolts.

Embodiment 23

The system of any of embodiments 20-22, wherein a sum of an AV interval at which the first pacing therapy is delivered relative to the determined atrial depolarization event, the blanking period, the first time period, and the second time period is less than an intrinsic AV-interval associated the patient.

Embodiment 24

The system of any of embodiments 20-23, wherein the first time period is between approximately 5 milliseconds and 20 milliseconds and the second time period is between approximately 5 milliseconds and 10 milliseconds.

Embodiment 25

A non-transitory computer readable medium storing instructions which cause a cardiac medical device to perform a method comprising:
sensing a cardiac signal of the patient;
determining an occurrence of one of an intrinsic and a paced atrial depolarization event of a current cardiac cycle in response to the sensed cardiac signal;
delivering a first pacing therapy during the current cardiac cycle in response to the determined occurrence of the depolarization event;

comparing an amplitude of the cardiac signal within the current cardiac cycle subsequent to the delivered first pacing therapy to a predetermined amplitude threshold; and
determining whether to deliver a second pacing therapy within the current cardiac cycle and subsequent to the delivered first pacing therapy in response to the comparing.

What is claimed:

1. A method for delivering a cardiac pacing therapy to a patient, comprising:
sensing a cardiac signal of the patient;
determining an occurrence of one of an intrinsic and a paced atrial depolarization event of a current cardiac cycle in response to the sensed cardiac signal;
delivering a first pacing therapy during the current cardiac cycle in response to the determined occurrence of the depolarization event, wherein the first pacing therapy comprising His Bundle pacing;
comparing an amplitude of the cardiac signal during a first time period within the current cardiac cycle subsequent to the delivered first pacing therapy to a predetermined amplitude threshold;
delivering a second pacing therapy within the current cardiac cycle and subsequent to the delivered first pacing therapy in response to the comparing,
wherein the second pacing therapy comprises ventricular pacing therapy; and
determining that intrinsic atrio-ventricular conduction is absent, wherein the His Bundle pacing is delivered having an AV delay between approximately 60 ms and 150 ms in response to intrinsic atrio-ventricular conduction being absent.

2. The method of claim 1, further comprising
delivering the second pacing therapy in response to the amplitude not being more negative than the predetermined amplitude threshold.

3. The method of claim 2, wherein the predetermined amplitude threshold is approximately −5 millivolts.

4. The method of claim 1, wherein the first time period is subsequent to a blanking period associated with the delivered first pacing therapy, delivering the second pacing therapy within a second time period subsequent to the first time period in response to the amplitude of the cardiac signal not being more negative than the amplitude threshold, wherein a sum of an AV interval at which the first pacing therapy is delivered relative to the determined atrial depolarization event, the blanking period, the first time period, and the second time period is less than an intrinsic AV interval associated with the patient.

5. The method of claim 4, wherein the sum of the AV interval at which the first pacing therapy is delivered relative to the determined atrial depolarization event, the blanking period, the first time period and the second time period is less than a sum of the AV interval at which the first pacing therapy is delivered relative to the determined atrial depolarization event and 40 ms in response to intrinsic atrio-ventricular conduction being absent.

6. The method of claim 5, wherein the first time period is between approximately 5 milliseconds and 20 milliseconds and the second time period is between approximately 5 milliseconds and 10 milliseconds.

7. The method of claim 1, wherein the first time period is subsequent to a blanking period associated with the delivered first pacing therapy, and wherein the method further comprises delivering the second pacing therapy within a second time period subsequent to the first time period in response to the cardiac signal not being more negative than the amplitude threshold.

8. The method of claim 7, wherein the predetermined amplitude threshold is approximately −5 millivolts.

9. The method of claim 7, wherein a sum of an AV interval at which the first pacing therapy is delivered relative to the determined atrial depolarization event, the blanking period, the first time period, and the second time period is less than an intrinsic AV-interval associated the patient.

10. The method of claim 9, wherein the first time period is between approximately 5 milliseconds and 20 milliseconds and the second time period is between approximately 5 milliseconds and 10 milliseconds.

11. A system for delivering a cardiac pacing therapy to a patient, comprising:
a first cardiac lead having a distal end;
at least one electrode positioned at the distal end of the first cardiac lead to sense a cardiac signal of the patient and deliver a first cardiac pacing therapy;
a second cardiac lead having a distal end;
at least one electrode positioned at the distal end of the second cardiac lead to deliver a second cardiac pacing therapy; and
a processor configured to:
determine an occurrence of one of an intrinsic and a paced atrial depolarization event of a current cardiac cycle in response to the sensed cardiac signal,
deliver a first pacing therapy via the at least one electrode of the first cardiac lead during the current cardiac cycle in response to the determined occurrence of the depolarization event,
compare an amplitude of the cardiac signal during a first time period within the current cardiac cycle subsequent to the delivered first pacing therapy to a predetermined amplitude threshold,
delivering a second pacing therapy within the current cardiac cycle and subsequent to the delivered first pacing therapy via the at least one electrode of the second cardiac lead in response to the comparing in response to the amplitude not being more negative than the predetermined amplitude threshold.

12. The system of claim 11, wherein the first pacing therapy comprises His Bundle pacing and the second pacing therapy comprises ventricular pacing therapy.

13. The system of claim 11, wherein the processor is configured to determine that intrinsic atrio-ventricular conduction is absent, wherein the first pacing therapy comprises His Bundle pacing and the second pacing therapy comprises ventricular pacing therapy, and wherein the His Bundle pacing is delivered having an AV delay between approximately 60 ms and 150 ms in response to intrinsic atrio-ventricular conduction being absent.

14. The system of claim 11, wherein the predetermined amplitude threshold is approximately −5 millivolts.

15. The system of claim 11, wherein the first time period is subsequent to a blanking period associated with the delivered first pacing therapy, and wherein the second pacing therapy is delivered within a second time period subsequent to the first time period, wherein a sum of an AV interval at which the first pacing therapy is delivered relative to the determined atrial depolarization event, the blanking period, the first time period, and the second time period is less than an intrinsic AV interval associated with the patient.

16. The system of claim 15, wherein the processor is configured to determine that intrinsic atrio-ventricular conduction is absent, wherein the first pacing therapy comprises His Bundle pacing and the second pacing therapy comprises ventricular pacing therapy, and wherein the sum of the AV interval at which the first pacing therapy is delivered relative to the determined atrial depolarization event, the blanking period, the first time period, and the second time period is less than a sum of the AV interval at which the first pacing therapy is delivered relative to the determined atrial depolarization event and 40 ms in response to intrinsic atrio-ventricular conduction being absent.

17. The system of claim 11, wherein the first time period is subsequent to a blanking period associated with the delivered first pacing therapy, and wherein the second pacing therapy is delivered within a second time period subsequent to the first time period, wherein the first pacing therapy comprises His Bundle pacing and the second pacing therapy comprises ventricular pacing therapy.

18. The system of claim 17, wherein the first time period is between approximately 5 milliseconds and 20 milliseconds and the second time period is between approximately 5 milliseconds and 10 milliseconds.

19. A method for delivering a cardiac pacing therapy to a patient, comprising:
sensing a cardiac signal of the patient;
determining an occurrence of one of an intrinsic and a paced atrial depolarization event of a current cardiac cycle in response to the sensed cardiac signal;
delivering a first pacing therapy during the current cardiac cycle in response to the determined occurrence of the depolarization event;
comparing an amplitude of the cardiac signal during a first time period within the current cardiac cycle subsequent to the delivered first pacing therapy to a predetermined amplitude threshold;
delivering a second pacing therapy in response to the amplitude not being more negative than the predetermined amplitude threshold.

20. The method of claim 19, wherein the first pacing therapy comprises His Bundle pacing and the second pacing therapy comprises ventricular pacing therapy.

21. The method of claim 19, wherein the predetermined amplitude threshold is approximately −5 millivolts.

22. The method of claim 19, wherein the first time period is subsequent to a blanking period associated with the delivered first pacing therapy, and wherein the second pacing therapy is delivered within a second time period subsequent to the first time period, wherein a sum of an AV interval at which the first pacing therapy is delivered relative to the determined atrial depolarization event, the blanking period, the first time period and the second time period is less than an intrinsic AV interval associated with the patient.

23. The method of claim 22, further comprising determining that intrinsic atrio-ventricular conduction is absent, wherein the first pacing therapy comprises His Bundle pacing and the second pacing therapy comprises ventricular pacing therapy, wherein the sum of the AV interval at which the first pacing therapy is delivered relative to the determined atrial depolarization event, the blanking period, the first time period and the second time period is less than a sum of the AV interval at which the first pacing therapy is delivered relative to the determined atrial depolarization event and 40 ms in response to intrinsic atrio-ventricular conduction being absent.

24. A method for delivering a cardiac pacing therapy to a patient, comprising:
sensing a cardiac signal of the patient;

determining an occurrence of one of an intrinsic and a paced atrial depolarization event of a current cardiac cycle in response to the sensed cardiac signal;

delivering a first pacing therapy during the current cardiac cycle in response to the determined occurrence of the depolarization event;

comparing an amplitude of the cardiac signal during a first time period within the current cardiac cycle subsequent to the delivered first pacing therapy to a predetermined amplitude threshold, wherein the first time period is subsequent to a blanking period associated with the delivered first pacing therapy;

delivering a second pacing therapy within the current cardiac cycle and subsequent to the delivered first pacing therapy in response to the amplitude of the cardiac signal not being more negative than the amplitude threshold, wherein the second pacing therapy is delivered within a second time period subsequent to the first time period, wherein a sum of an AV interval at which the first pacing therapy is delivered relative to the determined atrial depolarization event, the blanking period, the first time period, and the second time period is less than an intrinsic AV interval associated with the patient.

25. The method of claim 24, wherein the first pacing therapy comprises His Bundle pacing and the second pacing therapy comprises ventricular pacing therapy.

26. The method of claim 24, further comprising determining that intrinsic atrio-ventricular conduction is absent, wherein the first pacing therapy comprises His Bundle pacing and the second pacing therapy comprises ventricular pacing therapy, wherein the His Bundle pacing is delivered having an AV delay between approximately 60 ms and 150 ms in response to intrinsic atrio-ventricular conduction being absent.

27. The method of claim 24, wherein the predetermined amplitude threshold is approximately −5 millivolts.

28. The method of claim 24, wherein the first time period is between approximately 5 milliseconds and 20 milliseconds and the second time period is between approximately 5 milliseconds and 10 milliseconds.

29. A system for delivering a cardiac pacing therapy to a patient, comprising:
a first cardiac lead having a distal end;
at least one electrode positioned at the distal end of the first cardiac lead to sense a cardiac signal of the patient and deliver a first cardiac pacing therapy;
a second cardiac lead having a distal end;
at least one electrode positioned at the distal end of the second cardiac lead to deliver a second cardiac pacing therapy; and
a processor configured to:
determine an occurrence of one of an intrinsic and a paced atrial depolarization event of a current cardiac cycle in response to the sensed cardiac signal,
deliver a first pacing therapy via the at least one electrode of the first cardiac lead during the current cardiac cycle in response to the determined occurrence of the depolarization event,
compare an amplitude of the cardiac signal during a first time period within the current cardiac cycle subsequent to the delivered first pacing therapy to a predetermined amplitude threshold,
delivering a second pacing therapy within the current cardiac cycle and subsequent to the delivered first pacing therapy via the at least one electrode of the second cardiac lead in response to the comparing, and
determine that intrinsic atrio-ventricular conduction is absent, wherein the first pacing therapy comprises His Bundle pacing and the second pacing therapy comprises ventricular pacing therapy, and wherein the His Bundle pacing is delivered having an AV delay between approximately 60 ms and 150 ms in response to intrinsic atrio-ventricular conduction being absent.

30. The system of claim 29, wherein the first time period is subsequent to a blanking period associated with the delivered first pacing therapy, and delivering the second pacing therapy within a second time period subsequent to the first time period in response to the amplitude of the cardiac signal not being more negative than the amplitude threshold, wherein a sum of an AV interval at which the first pacing therapy is delivered relative to the determined atrial depolarization event, the blanking period, the first time period, and the second time period is less than an intrinsic AV interval associated with the patient.

31. The system of claim 30, wherein the sum of the AV interval at which the first pacing therapy is delivered relative to the determined atrial depolarization event, the blanking period, the first time period and the second time period is less than a sum of the AV interval at which the first pacing therapy is delivered relative to the determined atrial depolarization event and 39 ms in response to intrinsic atrio-ventricular conduction being absent.

32. The system of claim 29, wherein the first time period is between approximately 5 milliseconds and 20 milliseconds and the second time period is between approximately 5 milliseconds and 10 milliseconds.

33. The system of claim 29, wherein the first time period is subsequent to a blanking period associated with the delivered first pacing therapy, and delivering the second pacing therapy within a second time period subsequent to the first time period in response the amplitude of the cardiac signal not being more negative than the amplitude threshold, wherein the first pacing therapy comprises His Bundle pacing and the second pacing therapy comprises ventricular pacing therapy.

34. A system for delivering a cardiac pacing therapy to a patient, comprising:
a first cardiac lead having a distal end;
at least one electrode positioned at the distal end of the first cardiac lead to sense a cardiac signal of the patient and deliver a first cardiac pacing therapy;
a second cardiac lead having a distal end;
at least one electrode positioned at the distal end of the second cardiac lead to deliver a second cardiac pacing therapy; and
a processor configured to:
determine an occurrence of one of an intrinsic and a paced atrial depolarization event of a current cardiac cycle in response to the sensed cardiac signal,
deliver a first pacing therapy via the at least one electrode of the first cardiac lead during the current cardiac cycle in response to the determined occurrence of the depolarization event,
compare an amplitude of the cardiac signal during a first time period within the current cardiac cycle subsequent to the delivered first pacing therapy to a predetermined amplitude threshold, wherein the first time period is subsequent to a blanking period associated with the delivered first pacing therapy, deliver a second pacing therapy within the current cardiac cycle and subsequent to the delivered first pacing therapy via the at least one electrode of the second cardiac lead in response to the amplitude of the cardiac signal not being more negative than an amplitude threshold, wherein the second pacing therapy is delivered within a second time period subsequent to the first time period, wherein a sum of an AV interval at which the first pacing therapy is delivered relative to the determined atrial depolarization event, the blanking period, the first time period and the second time period is less than an intrinsic AV interval associated with the patient.

35. The system of claim 34, wherein the first pacing therapy comprises His Bundle pacing and the second pacing therapy comprises ventricular pacing therapy.

36. The system of claim 34, wherein the predetermined amplitude threshold is approximately −5 millivolts.

37. The system of claim 34, wherein the processor is configured to determine that intrinsic atrio-ventricular conduction is absent, wherein the first pacing therapy comprises His Bundle pacing and the second pacing therapy comprises ventricular pacing therapy, and wherein the sum of the AV interval at which the first pacing therapy is delivered relative to the determined atrial depolarization event, the blanking period, the first time period, and the second time period is less than a sum of the AV interval at which the first pacing therapy is delivered relative to the determined atrial depolarization event and 39 ms in response to intrinsic atrio-ventricular conduction being absent.

38. The system of claim 34, wherein the first time period is between approximately 5 milliseconds and 20 milliseconds and the second time period is between approximately 5 milliseconds and 10 milliseconds.

* * * * *